(12) United States Patent
Welch et al.

(10) Patent No.: US 6,613,924 B1
(45) Date of Patent: Sep. 2, 2003

(54) SILVER PRECURSORS FOR CVD PROCESSES

(75) Inventors: John T. Welch, Albany, NY (US); Silvana C. Ngo, Albany, NY (US); Kulbinder K. Banger, Albany, NY (US)

(73) Assignee: Research Foundation of State of New York, Albany, NY (US)

( * ) Notice: Subject to any disclaimer, the term of this patent is extended or adjusted under 35 U.S.C. 154(b) by 0 days.

(21) Appl. No.: 09/447,974

(22) Filed: Nov. 23, 1999

(65) Prior Publication Data (65)

(51) Int. Cl.[7] .............................. C07F 1/10; C07C 49/04
(52) U.S. Cl. ...................... 556/110; 556/113; 556/117; 556/112; 568/412; 568/579
(58) Field of Search ................... 556/110, 112, 556/113, 117; 568/579, 412

(56) References Cited

U.S. PATENT DOCUMENTS

| | | | |
|---|---|---|---|
| 4,880,670 A | 11/1989 | Erbil | 427/226 |
| 4,927,670 A | 5/1990 | Erbil | 427/255.3 |
| 4,948,623 A | 8/1990 | Beach et al. | 427/35 |
| 5,096,737 A | 3/1992 | Baum et al. | 427/38 |
| 5,220,044 A | 6/1993 | Baum et al. | 556/40 |

FOREIGN PATENT DOCUMENTS

| | | |
|---|---|---|
| JP | 05279221 | 11/1993 |
| JP | 05332717 | 12/1993 |
| JP | 07159312 | 6/1995 |
| JP | 08145927 | 6/1996 |

OTHER PUBLICATIONS

Gibson, D. et al.: Metal beta–diketone complexes. J. Chem. Soc. (A), vol. 3, pp. 367–689, 1970.*

Lin et al., "Surface–Selective Deposition of Palladium and Silver Films from Metal–Organic Precursors: A Novel Metal–Organic Chemical Vapor Deposition Redox Transmetalation Process" *J. Am. Chem. Soc.,* 115 11644–11645 (1993).

Chi et al., "Synthesis and Characterization of (β–Diketonato) silver Vinyltriethylsilane Compounds and Their Application to CVD of Silver Thin Films. Crystal Structure of the (2,2–Dimethyl–6,6,7,7,8,8,8–heptafluoro–3,5–octanedionato) silver Vinyltriethylsilane Dimer" *Organometallics* 15 2575–2578 (1996).

Li et al., "Electronic Structures of Copper(I) and Silver (I) β–Diketonate Complexes" *Inorganic Chemistry* 5040–5049 (1996).

Yuan et al., "A Binuclear bis (bis (dimethylphosphino) methane) disilver (I) complex with weakly bonded hexafluoroacetylacetonato ligands" *Can J. Chem.,* 1605–1609 (1994).

Bailey et al., "Synthesis and Characterization of 1,1,1,5,5,5–Hexafluoroacetylacetonato–(1,5–Cyclooctadiene) silver (I) Dimer. An unusual–β–Diketonate Coordination Mode" *Polyhedron,* 1785–1792 (1993).

* cited by examiner

*Primary Examiner*—Charanjit S. Aulakh
(74) *Attorney, Agent, or Firm*—Heslin Rothenberg Farley & Mesiti P.C.; Mary Louise Gioeni, Esq.

(57) ABSTRACT

Organosilver complexes with β-diketonates and neutral coordinating ligands are useful as silver precursors in chemical vapor deposition processes. The β-diketonates include 1,1,1,5,5,5-hexafluoro-2,4-pentanedionate (hfac), acetylacetonate (acac), 2,2,6,6-tetramethyl-3,5-heptanedionate (tmhd), 1,1,1-trifluoro-2,4-pentanedionate, (tfac), 2,2,7-trimethyl-3,5-octanedionate (tmod), 1,1,1-trifluoro-5,5-dimethyl-2,4-pentanedionate (tfh) 1,1,1,2,2,3,3,7,7,8,8,9,9,9-tetradecafluoro-4,6-nonanedionate (tdf). Neutral coordinating ligands include triphenylphosphine, tributylphosphine, pyridine, tetramethylethanediamine (TMEDA) and tetramethylpropanediamine (TMPDA).

2 Claims, No Drawings

SILVER PRECURSORS FOR CVD PROCESSES

BACKGROUND

Chemical vapor deposition (CVD) processes have been of increasing commercial importance over the past decade. A resurgence of interest in CVD of group II metals is due to efforts to reduce the size of device features as the microelectronics industry moves toward ultra large scale integration (ULSI). Use of group II metals, including silver, in interconnect structures having the submicron geometries required by ULSI is motivated by the lower resistivity of these metals. Chemical vapor deposition processes have an advantage over currently used physical vapor deposition processes such as sputtering and vacuum evaporation in the fabrication of submicron vertical interconnects because conformal layers of metals are more easily produced by CVD.

In chemical vapor deposition of metals, a volatile precursor, usually a complex of a metal with an organic ligand, serves as a source of the metal. The precursor is delivered to the substrate in the vapor phase and decomposed on the surface to release the metal. The precursor must exhibit sufficient thermal stability to prevent premature degradation or contamination of the substrate and at the same time facilitate easy handling. In some cases, the precursor must be depositable at a relatively low temperature in order to preserve the characteristics of the underlying layers previously formed. For example, deposition on a polymer substrate requires processing temperatures below the glass transition temperature of the polymer. Additionally, precursors for use in codeposition processes, where more than one metal is deposited, must have no detrimental effect on the coherent deposition of layers when used in the presence of other precursors.

Precursors for many metals are commercially available, including barium, strontium, and copper. However, there are few reports of organosilver complexes used as metal precursors for CVD, and these complexes have been used solely for the deposition of pure silver films. U.S. Pat. No. 4,948,623 to Beach discloses the use of a cyclopentadienyl-based silver precursor for the deposition of pure silver films. Chi et al, *Organonmetallics*, 1996,2575–2578, discusses the synthesis and CVD of a fluorinated β-diketonato silver(I) complex, with a silylated alkene as the coordinating ligand. Several Japanese patent applications, including JP 07133285, JP 07188256, and JP 08074055, disclose silver(I) fluorinated β-diketonato precursors with silylated olefins as coordinating ligands. The formation of silver films by CVD has proved to be difficult in comparison to other metals such as copper. The large atomic nucleus of silver may partly account for this difference. In addition, the large coordination sphere and low oxidation state of silver permits a higher coordination number relative to other metals, facilitating the formation and stability of dimeric compounds, and resulting in low volatility of the dimer. Hard soft acid base theory may also partly explain the poor performance of some silver precursors, which fragment and/or lose coordinating ligands during volatilization.

Thus, there is a lack of silver precursors having an attractive balance of properties for commercial use in CVD processes, either for the deposition of pure silver films or for codeposition of silver with other elements, although silver could be advantageously employed in a variety of applications. As discussed above, silver films could be utilized as low resistance interconnects for ULSI circuits. Layers containing phosphors for use in thin film electroluminescent (TFEL) displays, are commonly formed by a CVD process. Known phosphors are based on metal sulfides, activated by one or more dopants. While phosphors that emit red or yellow light of sufficient brightness are well-developed, there exists a need for blue-emitting phosphors for TFEL displays.

SUMMARY OF THE INVENTION

A class of organosilver complexes has now been discovered that are useful as silver precursors for CVD processes. The silver precursors of the present invention have the structure of formula I:

wherein
$L^1$ is a ligand of formula II;

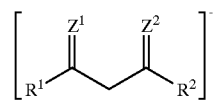

$R^1$ and $R^2$ are independently alkyl, substituted alkyl, aryl, arylalkyl, or fluoroalkyl;
$R^3$ is lower alkyl;
$Z^1$ and $Z^2$ are independently O, N or S;
n is 0 or 1;
$L^2$ is a neutral coordinating ligand chosen from $PR_3$, thiophene, pyridine, tetramethylethanediamine, (TMEDA), and tetramethylpropanediamine (TMPDA); and
R is $C_3$–$C_6$ alkyl, aryl or alkylaryl.

In one aspect, the present invention relates to a CVD process for the deposition of silver on a substrate comprising vaporizing a silver precursor of formula I, and decomposing the precursor on a substrate.

In another aspect, the present invention relates to a phosphor layer of a thin film electroluminescent device comprising a silver activator dopant. Preferably, the phosphor layer additionally comprises strontium sulfide and a copper coactivator dopant. The present invention also relates to a thin film electroluminescent display panel comprising a silver-doped phosphor, or a phosphor that comprises a silver activator dopant.

In yet another aspect, the present invention relates to a CVD process for the preparation of a phosphor layer of a thin film electroluminescent device comprising vaporizing at least one volatile non-silver metal precursor and a silver precursor of formula III,

wherein
$L^1$ is a ligand of formula II;

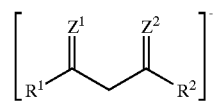

$R^1$ and $R^2$ are independently alkyl, substituted alkyl, aryl, arylalkyl, or fluoroalkyl;
$R^3$ is lower alkyl;

$Z^1$ and $Z^2$ are independently O, N or S;

n is 0 or 1;

$L^3$ is a neutral coordinating ligand chosen from $PR_3$, thiophene, pyridine, tetramethylethanediamine (TMEDA), tetramethylpropanediamine (TMPDA), vinyltriethylsilane (VTES), vinyltriethoxysilane (VTEXS) and 1,5 cyclooctadiene (COD); and R is $C_2$–$C_6$ alkyl, aryl or alkylaryl and decomposing at least one volatile non-silver metal precursor and the silver precursor on the substrate. A preferred non-silver metal is strontium; more preferably strontium and copper are the non-silver metals. The precursors are preferably vaporized under an atmosphere of a reactive gas, and more preferably under an atmosphere of hydrogen sulfide. In this case, hydrogen sulfide serves as a source of sulfur. Preferred β-diketonate ligands ($L^1$) of Formula III are: 1,1,1,5,5,5-hexafluoro-2,4-pentanedionate (hfac), acetylacetonate (acac), 2,2,6,6-tetramethyl-3,5-heptanedionate (tmhd), 1,1,1-trifluoro-2,4-pentanedionate (tfac), 2,2,7-trimethyl-3,5-octanedionate (tmod), 1,1,1-trifluoro-5,5-dimethyl-2,4-pentanedionate (tfh) and 1,1,1,2,2,3,3,7,7,8,8,9,9,9-tetradecafluoro-4,6-nonanedionate (tdf). For $L^3$, preferred neutral coordinating ligands are triphenylphosphine, tributylphosphine, triethylphosphine, pyridine, tetramethylethanediamine (TMEDA) tetramethylpropanediamine (TMPDA), vinyltriethylsilane (VTES), vinyltriethoxysilane (VTEXS) and 1,5 cyclooctadiene (COD). Preferred silver precursors are: Ag(acac)(PPh$_3$), Ag(hfac)(C$_5$H$_5$N), Ag(hfac)(PBu$_3$), Ag(hfac)(PPh$_3$), Ag(hfac)(TMEDA), Ag(hfac)(TMPDA), Ag(tmhd)(PBu$_3$), Ag(tmhd)(PPh$_3$), Ag(tmod)(PPh$_3$), Ag(tmod)(PEt$_3$), Ag(tmod)(PBu$_3$), Ag(hfac)(COD), Ag(tfac)(VTES), Ag(tfh)(VTES) and Ag(hfac)(VTEXS).

DETAILED DESCRIPTION OF THE INVENTION

Volatile silver precursors for use in chemical vapor deposition processes according to the present invention comprise three elements: a silver ion, Ag$^+$, an organic β-diketonate ligand, and a neutral coordinating ligand. The silver precursors have the structure of formula I:

 (I)

wherein $L^1$ is a ligand of formula II;

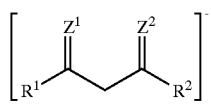   II $R^1$ and $R^2$ are independently alkyl, substituted alkyl, aryl, arylalkyl, or fluoroalkyl;

$R^3$ is lower alkyl;

$Z^1$ and $Z^2$ are independently O, N or S;

n is 0 or 1;

$L^2$ is a neutral coordinating ligand chosen from $PR_3$, thiophene, pyridine, tetramethylethanediamine, (TMEDA), and tetramethylpropanediamine (TMPDA); and R is $C_3$–$C_6$ alkyl, aryl or alkylaryl.

For $L^1$, preferred β-diketonate ligands of Formula II are: 1,1,1,5,5,5-hexafluoro-2,4-pentanedionate (hfac), acetylacetonate (acac), 2,2,6,6-tetramethyl-3,5-heptanedionate (tmhd), 1,1,1-trifluoro-2,4-pentanedionate (tfac), 2,2,7-trimethyl-3,5-octanedionate (tmod), 1,1,1-trifluoro-5,5-dimethyl-2,4-pentanedionate (tfh) and 1,1,1,2,2,3,3,7,7,8,8,9,9,9-tetradecafluoro-4,6-nonanedionate (tdf). For $L^2$, preferred neutral coordinating ligands are triphenylphosphine, tributylphosphine, pyridine, tetramethylethanediamine (TMEDA) and tetramethylpropanediamine (TMPDA). Preferred silver precursors of Formula I are: Ag(acac)(PPh$_3$), Ag(hfac)(C$_5$H$_5$N), Ag(hfac)(PBu$_3$), Ag(hfac)(PPh$_3$), Ag(hfac)(TMEDA), Ag(hfac)(TMPDA), Ag(tmhd)(PBu$_3$), Ag(tmhd)(PPh$_3$), Ag(tmod)(PPh$_3$) and Ag(tmod)(PBu$_3$).

The silver precursors of the present invention may be used in a CVD process to form a layer of silver metal, or of particular silver compounds, on a substrate. The silver-containing layers are useful in a variety of microelectronics applications, for example, to form interconnects.

Accordingly, the present invention also relates to a CVD process for depositing a silver-containing layer on a substrate. The method comprises the steps of vaporizing a silver complex or precursor of formula I, and decomposing the precursor on a substrate. For the CVD process of the present invention, the β-diketonate ligands, and neutral coordinating ligands described above are preferred. Specifically, for $L^1$, preferred β-diketonate ligands of Formula II are: 1,1,1,5,5,5-hexafluoro-2,4-pentanedionate (hfac), acetylacetonate (acac), 2,2,6,6-tetramethyl-3,5-heptanedionate (tmhd), 1,1,1-trifluoro-2, 4-pentanedionate (tfac), 2,2,7-trimethyl-3,5-octanedionate (tmod), 1,1,1-trifluoro-5,5-dimethyl-2,4-pentanedionate (tfh) and 1,1,1,2,2,3,3,7,7,8,8,9,9,9-tetradecafluoro-4,6-nonanedionate (tdf). For $L^2$, preferred neutral coordinating ligands are triphenylphosphine, tributylphosphine, pyridine, tetramethylethanediamine (TMEDA) and tetramethylpropanediamine (TMPDA). Preferred silver precursors of Formula I for use in the CVD process of the present invention are: Ag(acac)(PPh$_3$), Ag(hfac)(C$_5$H$_5$N), Ag(hfac)(PBu$_3$), Ag(hfac)(PPh$_3$), Ag(hfac)(TMEDA), Ag(hfac)(TMPDA), Ag(tmhd)(PPh$_3$), Ag(tmhd)(PBu$_3$), Ag(tmod)(PPh$_3$) and Ag(tmod)(PBu$_3$).

The CVD process of the present invention is also suitable for depositing layers which contain one or more metals in addition to silver. In this case, the deposition process is characterized in that for depositing layers containing metals other than silver, one or more metal precursors in addition to compounds of formula I are decomposed simultaneously or successively.

Typically, an apparatus for deposition from the vapor phase is pressure tight and can be evacuated. The substrate which is to be coated is to be introduced into this apparatus. Under reduced pressure, the silver precursor of formula I is vaporized. If desired, inert or reactive gas may be present in the apparatus in addition to the silver precursor in the vapor state.

The precursor(s) are typically continuously or intermittently introduced into the CVD apparatus in vapor form via a special line. In some cases the precursor(s) may be introduced into the apparatus together with the substrate which is to be coated and not vaporized until they are within the apparatus. A carrier gas may optionally be used to aid in transporting the metal complex into the apparatus. The vaporization of the metal complex can be promoted by heating and, if desired, by the addition of the carrier gas. The carrier gas may be reactive or inert. An inert gas commonly used in chemical vapor depositions is argon. Examples of reactive gases include hydrogen, oxygen, ozone, nitrogen dioxide, water vapor, ammonia and hydrogen sulfide.

If the silver precursor is decomposed under an atmosphere of an inert gas, for example, argon, silver-containing layers are typically deposited in which the metal is in essentially metallic form. The decomposition may also be carried out under a reactive gas atmosphere, including a reducing atmosphere, an oxidizing atmosphere, and a hydrolyzing or carbonizing atmosphere. A reducing atmosphere with hydrogen as the reactive gas is typically used for deposition of layers containing metals, for example, copper metal. Where the decomposition is carried out under an oxidizing atmosphere, for example, one containing oxygen, nitrogen dioxide or ozone, layers containing the metal in the form of an oxide are formed. It is also possible to operate in a hydrolyzing or carbonizing atmosphere, for instance, in the presence of water and/or carbon dioxide. The metal carbonate or hydroxide which is produced as an intermediate stage may be subsequently calcined to form the metal oxide. Use of ammonia as a reactive gas yields layers containing the metal in the form of a nitride, and use of hydrogen sulfide results in a layer containing metal sulfides.

Thermal decomposition from the vapor phase is usually performed so that the walls of the apparatus are kept cold and the substrate is heated to a temperature at which the desired layer is deposited on the substrate. The minimum temperature required for decomposition of the compound may be determined in each case by simple testing. Usually, the temperature to which the substrate is heated is above about 80° C.

The substrate may be heated in a conventional manner, for example, by resistance heating, inductive heating, or electric heating, or the substrates may be heated by radiation energy. Laser energy is particularly suitable for this. Laser heating is particularly advantageous in that lasers can be focused, and therefore can target limited areas on the substrate for heating.

An apparatus for thermal chemical vapor deposition is typically pressure tight such as are used in high vacuum techniques, as this process is typically carried out under reduced pressure. The apparatus may comprise gas lines which can be heated for carrying the precursor(s) or the inert or reactive gas, blockable gas inlets and outlets, and temperature measuring means. If decomposition is to be induced by radiation, a radiation source must also be present.

Decomposition of the substrate may be effected by known methods. In general, these are thermal decomposition, plasma-or radiation-induced decomposition and/or photolytic decomposition. For plasma-induced decomposition, a D.C. plasma, high-frequency plasma, microwave plasma or glow discharge plasma may be used. Alternately, photolytic decomposition may be effected by using a laser operating at a suitable wavelength.

The thickness of the layer deposited typically depends on the length of the deposition, on the partial pressure in the gas phase, on the flow rate of the gas and on the decomposition temperature. Depending on the desired layer thickness, a person skilled in the art can readily determine the time and deposition temperature required to produce a layer of a given thickness by simple tests.

The present invention also relates to a phosphor layer of a thin film electroluminescent device; the phosphor layer contains a silver activator dopant as a luminescent center. The phosphor layer is formed from at least one host matrix material which is doped with silver and, if desired, at least one other activator, such that the resulting phosphor is capable of emitting light in the range of infrared, visible or ultraviolet light. The host matrix material in the phosphor layer is typically a metal sulfide. In particular, alkaline earth sulfides, such as MgS, CaS, SrS, BaS, ZnS, and CdS are commonly used. It may be desirable to include a coactivator dopant such as copper, sodium, potassium, zinc, chlorine or fluorine, in addition to a silver dopant. A phosphor layer according to the present invention is preferably composed of strontium sulfide as a host matrix with copper and silver as activator dopants; such a phosphor emits blue light.

A thin film electroluminescent display panel in accordance with the present invention typically includes a glass substrate which supports a transparent electrode such as indium tin oxide (ITO). Over the electrode layer is a layer of a dielectric material such as barium tantalate ($BaTa_2O_6$), strontium titanate ($SrTiO_3$), barium titanate ($BaTiO_3$), or aluminum titanate oxide [$Al_2O_3/TiO_3$ (ATO)]. One or more electroluminescent phosphor layers separated by layers of dielectric material such as described above are formed. Typically the phosphor layers are of different compositions in order to emit light of different wavelengths. For example, red is emitted by CaS:Eu and ZnS:Sm, green by ZnS:Tb, and yellow by ZnS:Mn. An opaque electrode layer composed of aluminum is typically formed over the phosphor layer(s).

The present invention also relates to a CVD process for the preparation of a phosphor layer of a thin film electroluminescent device comprising silver as an activator dopant. The process comprises vaporizing at least one volatile non-silver metal precursor and a silver precursor of formula III:

wherein
L$^1$ is a ligand of formula II;

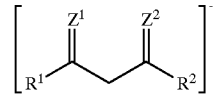

R$^1$ and R$^2$ are independently alkyl, substituted alkyl, aryl, arylalkyl, or fluoroalkyl;
R$^3$ is lower alkyl;
Z$^1$ and Z$^2$ are independently O, N or S;
n is 0 or 1;
L$^3$ is a neutral coordinating ligand chosen from PR$_3$, thiophene, pyridine, tetramethylethanediamine (TMEDA), tetramethylpropanediamine (TMPDA), vinyltriethylsilane (VTES), vinyltriethoxysilane (VTEXS) and 1,5 cyclooctadiene (COD); and
R is $C_2$–$C_6$ alkyl, aryl or alkylaryl
and decomposing the non-silver metal precursor(s) and the silver precursor on the substrate. A preferred non-silver metal is strontium; more preferably, copper is used in addition to silver and strontium. A preferred host matrix material is strontium sulfide. The vaporization and decomposition may be simultaneous or sequential, and may be performed under an atmosphere of a reactive or inert carrier gas. A reactive gas is preferably used; more preferably, hydrogen sulfide is used as a source of sulfur. The non-silver metal(s) may be deposited from one or more organometallic precursors such as metal β-diketonate complexes. Strontium sulfide may be deposited from Sr(tmhd)$_2$ under an atmosphere of H$_2$S. Copper is preferred as a coactivator dopant; a commercially available copper precursor is Cu(tmod)$_2$.

For the CVD process of the present invention for the preparation of a silver-doped phosphor layer of a thin film electroluminescent device, preferred β-diketonate ligands (L$^1$) of Formula III are: 1,1,1,5,5,5-hexafluoro-2,4-pentanedionate (hfac), acetylacetonate (acac), 2,2,6,6- tetramethyl-3,5-heptanedionate (tmhd), 1,1,1-trifluoro-2,4-pentanedionate (tfac), 2,2,7-trimethyl-3,5-octanedionate (tmod), 1,1,1-trifluoro-5,5-dimethyl-2,4-pentanedionate (tfh) and 1,1,1,2,2,3,3,7,7,8,8,9,9,9-tetradecafluoro-4,6-nonanedionate (tdf). For $L^3$, preferred neutral coordinating ligands are triphenylphosphine, tributylphosphine, triethylphosphine, pyridine, tetramethylethanediamine (TMEDA) tetramethylpropanediamine (TMPDA), vinyltriethylsilane (VTES), vinyltriethoxysilane (VTEXS) and 1,5 cyclooctadiene (COD). Preferred silver precursors are: Ag(acac)(PPh$_3$), Ag(hfac)(C$_5$H$_5$N), Ag(hfac)(PBu$_3$), Ag(hfac)(PPh$_3$), Ag(hfac)(TMEDA), Ag(hfac)(TMPDA), Ag(tmhd)(PBu$_3$), Ag(tmhd)(PPh$_3$), Ag(tmod)(PPh$_3$), Ag(tmod)(PEt$_3$), Ag(tmod)(PBu$_3$), Ag(hfac)(COD), Ag(tfac)(VTES), Ag(tfh)(VTES) and Ag(hfac)(VTEXS).

EXAMPLES

Example 1

Ag(hfac)

Under anaerobic conditions and in the absence of light, a 250 mL Schlenk flask equipped with a magnetic stirrer was charged with anhydrous THF (30 mL), and Ag$_2$O (2.24 g, 9.6 mmol). 1,1,1,5,5,5-hexafluoro-2,4-pentanedione (hfac) (2.7 mL, 19.2 mmol) was then added dropwise into the reaction flask whilst stirring. After 1 hour, the mixture was then filtered into a second flask to remove any unreacted silver oxide. Removal of the solvent in vacuo gave an off-white solid.

Example 2

Ag(hfac)(COD) Preparation I

Under anaerobic conditions and in the absence of light, a 50 mL Schlenk flask equipped with a magnetic stirrer was charged with anhydrous toluene (20 mL) and COD (0.14 mL, 1.14 mmol). Freshly prepared Ag(hfac) (0.36 g, 1.14 mmol) was added slowly and allowed to react for 30–45 minutes. The reaction mixture was then filtered via cannula into a second flask to remove any solid impurities. Removal of solvent yielded Ag(hfac)(COD) as a white crystalline material.

Example 3

Ag(hfac)(COD) Preparation II

Under anaerobic conditions and in the absence of light, a 100 mL Schlenk flask equipped with a magnetic stirrer was charged with anhydrous THF (16 mL), Ag$_2$O (0.50 g, 2.17 mmol), and 1,5-cyclooctadiene (COD) (0.53 mL, 4.32 mmol). 1,1,1,5,5,5-Hexafluoro-2,4-pentanedione (hfac) (0.61 mL, 4.31 mmol) was then added dropwise into the reaction flask whilst stirring. The mixture was allowed to react for 4 hours after which the reaction was essentially complete. The volatile components were then removed in vacuo to yield the crude product. The product was extracted with toluene and filtered to remove any unreacted Ag$_2$O. Removal of solvent yielded the product as a white crystalline material.

Example 4

Ag(hfac)(COD) Preparation III

In a 100 mL single neck flask, silver nitrate, (AgNO$_3$), (0.37 g, 2.174 mmol) was dissolved in 5 mL of distilled, deoxygenated water under a flow of nitrogen gas. Addition of 1,5-cyclooctadiene (0.27 mL, 2.174 mmol), and sodium 1,1,1,5,5,5-hexafluoro-2,4-pentanedione (0.5 g, 2.174 mmol) respectively resulted in the precipitation of a white solid. Filtration and subsequent drying in vacuo gave the silver complex.

Example 5

Ag(hfac)(VTES)

Under anaerobic conditions a 250 mL Schlenk flask equipped with a magnetic stirrer was charged with anhydrous diethyl ether (50 mL), Ag$_2$O (0.63 g, 2.7 mmol), and vinyltriethylsilane (VTES) (1.00 mL, 5.4 mmol). An etherate solution of 1,1,1,5,5,5-hexafluoro-2,4-pentanedione (hfac) (0.77 mL, 5.4 mmol) was then added dropwise to the reaction flask whilst stirring. The mixture was allowed to react for 5 hours after which the reaction was essentially complete. The reaction solution was then filtered to remove any unreacted Ag$_2$O. The volatile components were then removed in vacuo to yield the product as a pale yellow oil.

Example 6

Ag(hfac)(VTEXS)

Under anaerobic conditions a 250 mL Schlenk flask equipped with a magnetic stirrer was charged with anhydrous diethyl ether (50 mL), Ag$_2$O, (0.58 g, 2.51 mmol) and vinyltriethoxysilane (VTEXS) (1.10 mL, 5.22 mmol). An etherate solution of 1,1,1,5,5,5-hexafluoro-2,4-pentanedione (hfac) (0.72 mL, 5.09 mmol) was then added dropwise to the reaction flask whilst stirring. The mixture was allowed to react for 5 hours after which the reaction was essentially complete. The reaction solution was then filtered to remove any unreacted Ag$_2$O. The volatile components were then removed in vacuo to yield the product as a pale yellow oil.

Example 7

Ag(hfac)(C$_5$H$_5$N) Preparation I

Under anaerobic conditions and in the absence of light, a 250 mL Schlenk flask equipped with a magnetic stirrer was charged with anhydrous toluene (20 mL) and C$_5$H$_5$N (0.13 g, 1.59 mmol). Freshly prepared Ag(hfac) (0.5 g, 1.59 mmol) was added slowly and allowed to react for 30–45 minutes. The reaction mixture was then filtered via cannula into a second flask to remove any solid impurities. Removal of solvent yielded Ag(hfac)(C$_5$H$_5$N) as a white crystalline material.

Example 8

Ag(Hfac)(C$_5$H$_5$N) Preparation II

Under an inert atmosphere, 1,1,1,5,5,5-hexafluoro-2,4-pentanedione (hfac) (2.3 mL, 16 mmol) was added to a stirring slurry of Ag$_2$O (1.8 g, 7.8 mmol) in THF (32 mL). The mixture was stirred for 2.5 hours after which volatile components were removed in vacuo. The residue was dissolved in toluene, (21 mL) stirred for 1 hour and then filtered. Pyridine (C$_5$H$_5$N) (1.3 mL, 16 mmol) was added to the filtrate and the solution stirred for one hour. Removal of volatiles afforded the silver complex as an off-white solid.

Example 9

Ag(hfac)(PPh$_3$) Preparation I

Under anaerobic conditions and in the absence of light, a 250 mL Schlenk flask equipped with a magnetic stirrer was charged with anhydrous diethyl ether (10 mL) and Ag(hfac)(COD) (0.53 g, 1.26 mmol). Triphenylphosphine, (0.33 g, 1.26 mmol) dissolved in dry diethyl ether, (5 mL) was added slowly and allowed to react for 3 hours. Removal of the solvent and subsequent washing with pentane afforded the product, Ag(hfac)(PPh$_3$) as an off white solid.

Example 10

Ag(hfac)(PPh$_3$) Preparation II

Under anaerobic conditions and in the absence of light, a 250 mL Schlenk flask equipped with a magnetic stirrer was charged with anhydrous diethyl ether (10 mL), Ag$_2$O (0.51 g, 2.20 mmol), and triphenylphosphine (PPh$_3$) (1.16 g, 4.42 mmol). 1,1,1,5,5,5-Hexafluoro-2-,4-pentanedione (hfac) (0.63 mL, 4.42 mmol) was then added dropwise into the reaction flask whilst stirring. The mixture was allowed to react for 3 hours after which the reaction was essentially complete. The volatile components were then removed in vacuo to yield the crude product. The product was washed with pentane, extracted with toluene and filtered to remove any unreacted Ag$_2$O. Removal of solvent yielded the product as a gray-colored, crystalline material.

Example 11

Ag(hfac)(PBU$_3$)

In a 100 mL single neck flask, silver nitrate (AgNO$_3$) (0.37 g, 2.174 mmol) was dissolved in 5 mL of distilled, deoxygenated water under a flow of nitrogen gas. Addition of tri-n-butylphosphine (0.44 g, 2.174 mmol), and sodium 1,1,1,5,5,5-hexafluoro-2-,4-pentanedione (0.5 g, 2.174 mmol), respectively, resulted in the precipitation of an oily yellow product. Evaporation of volatile components in vacuo gave the silver complex.

Example 12

Ag(hfac)(PBu$_3$) Preparation II

Under an inert atmosphere, 1,1,1,5,5,5-hexafluoro-2,4-pentanedione (hfac) (1.8 mL, 13 mmol) was added to a stirring slurry of Ag$_2$O (1.5 g, 6.4 mmol) in diethyl ether (40 mL). The mixture was stirred for 30 minute, then tri-n-butylphosphine (3.4 mL, 13 mmol) was added. The mixture was stirred for 4 hours and then filtered. Removal of volatiles afforded the silver complex as a brown soft solid.

Example 13

Ag(hfac)(TMEDA)

Under anaerobic conditions and in the absence of light, a 250 mL Schlenk flask equipped with a magnetic stirrer was charged with anhydrous diethyl ether (10 mL), Ag$_2$O (0.63 g, 2.73 mmol) and tetramethylethanediamine (TMEDA) (0.83 mL, 5.50 mmol). 1,1,1,5,5,5-Hexafluoro-2-,4-pentanedione (hfac) (0.78 mL, 5.51 mmol) was then added dropwise into the reaction flask whilst stirring. The mixture was allowed to react for 3 hours after which the reaction was essentially complete. The volatile components were then removed in vacuo to yield the crude product. The product was washed with pentane, extracted with toluene and filtered to remove any unreacted Ag$_2$O. Removal of solvent yielded the product as a light yellow-colored, crystalline material.

Example 14

Ag(hfac)(TMEDA)

Under anaerobic conditions and in the absence of light, a 250 mL Schlenk flask equipped with a magnetic stirrer was charged with anhydrous toluene (50 mL) and tetramethylethanediamine (TMEDA) (0.15 mL, 0.99 mmol). Freshly prepared Ag$_2$(hfac)$_2$(H$_2$O) (0.32 g, 0.49 mmol) was added slowly and allowed to react for approximately 1 hour. The reaction mixture was then filtered via cannula into a second flask to remove any solid impurities. Removal of solvent yielded Ag(hfac)(TMEDA) as a light yellow colored, crystalline material.

Example 15

Ag(hfac)(TMPDA)

Under anaerobic conditions and in the absence of light, a 250 mL Schlenk flask equipped with a magnetic stirrer was charged with anhydrous toluene (50 mL) and tetramethylpropanediamine (TMPDA) (0.16 mL, 0.96 mmol). Freshly prepared Ag$_2$(hfac)$_2$(H$_2$O) (0.31 g, 0.47 mmol) was added slowly and allowed to react for approximately 1 hour. The reaction mixture was then filtered via cannula into a second flask to remove any solid impurities. Removal of solvent and subsequent washing with dry hexane afforded Ag(hfac)(TMPDA) as a brown-colored, crystalline material.

Example 16

Ag(tfac)

Under anaerobic conditions and in the absence of light, a 250 mL Schlenk flask equipped with a magnetic stirrer was charged with anhydrous diethyl ether (10 mL) and Ag$_2$O (0.54 g, 2.32 mmol). 1,1,1-Trifluoro-2,4-pentanedione (tfac) (0.57 mL, 4.7 mmol) was then added dropwise into the reaction flask whilst stirring. After 1 hour, the reaction mixture was almost clear and a grey precipitate has been formed. Removal of the solvent in vacuo and subsequent washing with pentane and drying yielded the product as an off-white solid.

Example 17

Ag(tfac)(VTES)

Under anaerobic conditions a 250 mL Schlenk flask equipped with a magnetic stirrer was charged with anhydrous diethyl ether (50 mL), Ag$_2$O (0.41 g, 1.79 mmol) and vinyltriethylsilane (VTES) (0.66 mL, 3.56 mmol). An etherate solution of 1,1,1-trifluoro-2-,4-pentanedione (tfac) (0.44 mL, 3.66 mmol) was then added drop wise to the reaction flask whilst stirring. After 3 hours, a grey precipitate was observed. The volatile components were then removed in vacuo to yield the crude material. The product was isolated by extraction with dry toluene and filtered to remove any unreacted Ag$_2$O. Removal of the solvent afforded the complex as white solid.

Example 18

Ag(tfh)(VTES)

Under anaerobic conditions a 250 mL Schlenk flask equipped with a magnetic stirrer was charged with anhydrous diethyl ether (50 mL), Ag$_2$O (0.41 g, 1.79 mmol) and vinyltriethylsilane (VTES) (0.66 mL, 3.56 mmol). An etherate solution of 1,1,1-trifluoro-5,5-dimethyl-2,4-pentanedione (tfh) (0.63 mL, 3.60 mmol) was then added dropwise to the reaction flask whilst stirring. After 3 hours, a grey precipitate was observed. The volatile components were then removed in vacuo to yield the crude material. The product was isolated by extraction with dry toluene and filtered to remove any unreacted Ag$_2$O. Concentration of the organic layer and drying afforded the complex as white solid.

Example 19

Ag(tmhd)

Under an inert atmosphere, a stirring slurry of silver nitrate (AgNO$_3$) (0.42 g, 2.5 mmol) in acetonitrile (0.14 mL) and methanol (5 mL) was cooled to 0° C. To this was added a solution of tmhd (0.55 mL, 2.6 mmol) and triethylamine (0.35 mL, 2.5 mmol) in methanol (5 mL). The mixture was stirred at 0° C. for 1 hour and then filtered quickly. The white-colored silver complex was washed with methanol and dried in vacuo.

Example 20

Ag(tmhd)(PPh$_3$) Preparation I

In the absence of light, triphenylphosphinesilverchloride (PPh$_3$AgCl) (4.05 g, 10 mmol) was vigorously stirred with a benzene/toluene solution of thallium(I) 2,2,6,6-tetramethyl-3,5-heptanedionate, (3.87 g, 10 mmol) for at least one hour. The reaction mixture was then filtered via cannula into a second Schlenk flask. The volatile components were then removed under high vacuum to leave behind a white residue. Recrystallization from benzene afforded white, light sensitive crystals.

Example 21

Ag(tmhd)(PPh$_3$) Preparation II

In a 50 mL single neck flask, silver nitrate (AgNO$_3$) (0.52 g, 3.06 mmol) and triphenylphosphine (PPh$_3$) (0.80 g, 3.06 mmol) was dissolved in diethyl ether (15 mL) under a flow of nitrogen gas for 1 hour. Sodium 2,2,6,6-tetramethyl-3,5-heptanedionate (0.63 g, 3.06 mmol) dissolved in anhydrous diethyl ether (10 mL) was added to the reaction mixture and allowed to react for 24 hours. The volatile components were then removed in vacuo to yield the crude product. Addition of toluene (30 mL) followed by filtration and evaporation in vacuo afforded the silver complex.

Example 22

Ag(tmhd)(PPh$_3$) Preparation III

Under an inert atmosphere, a stirring slurry of Ag(tmhd) (0.21 g, 0.72 mmol) and triphenylphosphine (0.19 g, 0.71 mmol) in toluene (10 mL) was cooled to 0° C. The mixture was stirred at 0° C. for 1 hour, after which the toluene was removed in vacuo, affording the silver complex as an off-white solid.

Example 23

Ag(tmhd)(PBu$_3$)

Under an inert atmosphere, tri-n-butylphosphine (0.15 mL, 0.57 mmol) was added to a stirring slurry of Ag(tmhd) (0.16 g, 0.55 mmol) in toluene (6 mL) at 0° C. The mixture was stirred at 0° C. for 1 hour, after which the toluene was removed in vacuo, affording the silver complex as a brown oily liquid.

Example 24

Ag(tmod)

Under an inert atmosphere, a stirring slurry of AgNO$_3$ (0.51 g, 3.0 mmol) in acetonitrile (0.17 mL) and methanol (6 mL) was cooled to 0 C. To this was added a solution of tmod (0.59 g, 3.2 mmol) and triethylamine (0.42 mL, 3.0 mmol) in methanol (6 mL). The mixture was stirred at 0° C. for 1 hour and then filtered quickly. The white-colored silver complex was washed with methanol and dried in vacuo.

Example 25

Ag(tmod)(PPh$_3$)

Under an inert atmosphere, triphenylphosphine (0.14 g, 0.53 mmol) was added to a stirring slurry of Ag(tmod) (0.16 g, 0.55 mmol) in toluene (12 mL) at 0° C. The mixture was stirred at 0° C. for 1 hour, after which the toluene was removed in vacuo. The residue was washed with pentane affording the silver complex as a gray solid.

Example 26

Ag(tmod)(PBu$_3$)

Under an inert atmosphere, tri-n-butylphosphine (0.14 mL, 0.53 mmol) was added to a stirring slurry of Ag(tmod) (0.16 g, 0.55 mmol) in toluene (12 mL) at 0° C. The mixture was stirred at 0° C. for 1 hour, after which the toluene was removed in vacuo, affording the silver complex as a black oily liquid.

Example 27

Ag(tmod)(PEt$_3$)

Under an inert atmosphere, triethylphosphine (0.10 mL, 0.68 mmol) was added to a stirring slurry of Ag(Tmod) (0.20 g, 0.69 mmol) in toluene (15 mL) at 0° C. The mixture was stirred at 0° C. for 1 hour, after which the toluene was removed in vacuo, affording the silver complex as a black oily liquid.

Example 28

Ag(acac)(PPh$_3$)

In the absence of light, triphenylphosphinesilverchloride (PPh$_3$AgCl) (4.05 g, 10 mmol) was vigorously stirred with a benzene/toluene solution of Thallium(I)acetylacetonate, (3.03 g, 10 mmol) for at least one hour. The reaction mixture was then filtered via cannula into a second Schlenk flask. The volatile components were then removed under high vacuum to leave behind a white residue. Recrystallization from benzene afforded white, light sensitive crystals.

Chemical Vapor Deposition of Silver

Silver films were deposited on fragments of aluminum-titanium-oxide (ATO) on glass and silicon wafers, using a silver precursor of composition Ag(hfac)(PBu$_3$). A cold wall stainless steel single wafer CVD reactor was employed for the depositions. The wafers were loaded into the chamber via a load lock system, placed on a resistively heated stainless steel pedestal bearing a quartz plate and heated to 350° C. under a flowing hydrogen ambient atmosphere. The actual temperature of the wafer was measured via a thermocouple contacting the top side of the wafer. The system pressure was then reduced to the desired deposition pressure of 500 mTorr. The pressure was maintained throughout the time of the deposition using an automated throttle valve.

A source of the precursor was maintained at 165° C. The precursor was delivered to the reactor by means of an argon carrier gas bubbler at a flow rate of 80 sccm at approximately 500 mTorr. After the deposition, the carrier gas flow was terminated, the source was closed to the reactor, and the chamber was evacuated to less than 20 mTorr and then flushed with nitrogen gas. The heater was allowed to cool under a flow of nitrogen. The test wafers were retrieved from the reactor through the door of the reactor.

What is claimed:

1. A compound of formula I:

 (I)

wherein $L^1$ is a ligand of formula II;

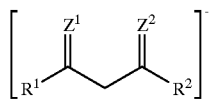

$R^1$ and $R^2$ are independently alkyl, substituted alkyl, aryl, arylalkyl, or fluoroalkyl;

$Z^1$ and $Z^2$ are independently O, N or S;

n is 0;

$L^2$ is a neutral coordinating ligand chosen from $PR_3$, thiophene, pyridine, tetramethylethanediamine, (TMEDA), and tetramethylpropanediamine (TMPDA); and R is $C_3$–$C_6$ alkyl, aryl or alkylaryl.

2. A silver precursor, according to claim 1, wherein $L^1$ is chosen from 1,1,1,5,5,5-hexafluoro-2,4-pentanedionate (hfac), acetylacetonate (acac), 2,2,6,6-tetramethyl-3,5-heptanedionate (tmhd), 1,1,1-trifluoro-2,4-pentanedionate, (tfac), 2,2,7-trimethyl-3,5-octanedionate (tmod), 1,1,1-trifluoro-5,5-dimethyl-2,4-pentanedionate (tfh) and 1,1,1,2,2,3,3,7,7,8,8,9,9,9-tetradecafluoro-4,6-nonanedionate (tdf).

* * * * *

UNITED STATES PATENT AND TRADEMARK OFFICE
CERTIFICATE OF CORRECTION

PATENT NO.    : 6,613,924 B1
DATED         : September 2, 2003
INVENTOR(S)   : Welch et al.

It is certified that error appears in the above-identified patent and that said Letters Patent is hereby corrected as shown below:

Title page,
Item [73], Assignee, delete "Research Foundation of State of New York" and insert
-- The Research Foundation of State University of New York --

Signed and Sealed this

Twenty-eighth Day of September, 2004

JON W. DUDAS
*Director of the United States Patent and Trademark Office*